(12) United States Patent
Giafferi et al.

(10) Patent No.: US 8,092,553 B2
(45) Date of Patent: Jan. 10, 2012

(54) COMPOSITION FOR THE OXIDATION DYEING OF KERATIN FIBERS COMPRISING PARA-AMINOPHENOL, DIPROPYLENE GLYCOL AND AT LEAST ONE ADDITIONAL DYE PRECURSOR

(75) Inventors: Marie Giafferi, Villemomble (FR); Marie-Pascale Audousset, Asnieres (FR); Isabelle Schlosser, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,468

(22) Filed: Dec. 18, 2009

(65) Prior Publication Data
US 2010/0154139 A1 Jun. 24, 2010

Related U.S. Application Data

(60) Provisional application No. 61/150,450, filed on Feb. 6, 2009.

(30) Foreign Application Priority Data

Dec. 19, 2008 (FR) ...................................... 08 07306

(51) Int. Cl.
A61Q 5/10 (2006.01)
(52) U.S. Cl. .............. 8/405; 8/406; 8/408; 8/410; 8/411; 8/412; 8/421; 8/435
(58) Field of Classification Search .............. 8/405, 406, 8/408, 410, 411, 412, 421, 435
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,826,681 A | 5/1989 | Jacquet et al. | |
| 4,845,293 A | 7/1989 | Junino et al. | |
| 5,021,066 A | 6/1991 | Aeby et al. | |
| 5,259,849 A | 11/1993 | Grollier et al. | |
| 5,364,414 A | 11/1994 | Lang et al. | |
| 5,817,155 A | 10/1998 | Yasuda et al. | |
| 6,010,541 A | 1/2000 | De La Mettrie | |
| 6,074,439 A * | 6/2000 | De La Mettrie et al. | 8/411 |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,251,378 B1 | 6/2001 | Laurent et al. | |
| 6,260,556 B1 | 7/2001 | Legrand et al. | |
| 6,277,154 B1 | 8/2001 | Lorenz | |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,645,258 B2 | 11/2003 | Vidal et al. | |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |
| 7,135,046 B2 | 11/2006 | Audousset | |
| 7,153,331 B2 | 12/2006 | Desenne et al. | |
| 7,217,298 B2 | 5/2007 | Legrand et al. | |
| 7,285,137 B2 | 10/2007 | Vidal et al. | |
| 7,442,215 B2 | 10/2008 | Audousset et al. | |
| 7,458,993 B2 | 12/2008 | Cottard et al. | |
| 7,494,513 B2 | 2/2009 | Kravtchenko et al. | |
| 7,575,605 B2 | 8/2009 | Legrand | |
| 7,651,533 B2 | 1/2010 | Legrand | |
| 7,651,536 B2 | 1/2010 | Cottard et al. | |
| 7,740,663 B2 | 6/2010 | De La Mettrie et al. | |
| 7,766,977 B2 | 8/2010 | Cottard et al. | |
| 7,799,095 B2 | 9/2010 | Mario et al. | |
| 2002/0189034 A1 | 12/2002 | Kitabata et al. | |
| 2003/0064494 A1 | 4/2003 | Kumar et al. | |
| 2003/0190297 A1 | 10/2003 | Narasimham et al. | |
| 2003/0226217 A1 | 12/2003 | Bowes et al. | |
| 2004/0103488 A1 | 6/2004 | Yamashita et al. | |
| 2004/0105830 A1 | 6/2004 | Boswell et al. | |
| 2004/0181883 A1 | 9/2004 | Legrand et al. | |
| 2004/0221400 A1 | 11/2004 | Cotteret et al. | |
| 2004/0226110 A1 | 11/2004 | Legrand | |
| 2004/0235700 A1 | 11/2004 | Legrand et al. | |
| 2005/0129652 A1 | 6/2005 | Keller et al. | |
| 2005/0165705 A1 | 7/2005 | Lauper et al. | |
| 2005/0196367 A1 | 9/2005 | Ohta et al. | |

(Continued)

FOREIGN PATENT DOCUMENTS

CA 1 268 421 5/1990

(Continued)

OTHER PUBLICATIONS

French Search Report for FR 0807306, dated Aug. 13, 2009.

(Continued)

*Primary Examiner* — Eisa Elhilo
(74) *Attorney, Agent, or Firm* — Finnegan, Henderson, Farabow, Garrett & Dunner, LLP

(57) ABSTRACT

The present disclosure relates to a composition for the oxidation dyeing of keratin fibers, for example, human keratin fibers such as the hair, intended to be mixed at the time of use with an oxidizing agent, comprising: A) at least one oxidation base chosen from para-aminophenols and the addition salts thereof with an acid; B) at least one additional dye precursor different from the at least one oxidation base defined in A); and C) dipropylene glycol; wherein: the at least one oxidation base is present in an amount of greater than or equal to 1.5% by weight, relative to the total weight of the composition; and the dipropylene glycol is present in an amount of greater than or equal to 3.5% by weight, relative to the total weight of the composition.

20 Claims, No Drawings

U.S. PATENT DOCUMENTS

| | | |
|---|---|---|
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |
| 2010/0162492 A1 | 7/2010 | Hercouet et al. |
| 2010/0175705 A1 | 7/2010 | Hercouet et al. |
| 2010/0186177 A1 | 7/2010 | Hercouet et al. |
| 2010/0199441 A1 | 8/2010 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 198 42 071 | 3/2000 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 193 471 | 9/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 449 512 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 A2 | 3/2008 |
| EP | 1 927 377 | 6/2008 |
| EP | 1 944 009 | 7/2008 |
| EP | 2 005 939 | 12/2008 |
| EP | 2 011 473 | 1/2009 |
| EP | 2 011 474 | 1/2009 |
| EP | 2 018 848 | 1/2009 |
| EP | 2 047 841 | 4/2009 |
| EP | 2 072 034 | 6/2009 |
| EP | 2 072 035 | 6/2009 |
| EP | 2 072 036 | 6/2009 |
| EP | 2 198 842 | 6/2010 |
| EP | 2 198 843 | 6/2010 |
| EP | 2 198 849 | 6/2010 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 A1 | 8/2008 |
| FR | 2 912 906 | 8/2008 |
| FR | 2 915 886 A1 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| FR | 2 940 054 | 6/2010 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |

| | | |
|---|---|---|
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 A1 | 8/2008 |
| WO | WO 2008/138844 | 11/2008 |
| WO | WO 2009/010883 | 1/2009 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

English language abstract of FR 2 912 904 A1, Aug. 29, 2008.
English language abstract of FR 2 915 886 A1, Nov. 14, 2008.
English language abstract of JP 2001-233748, Aug. 28, 2001.
English language abstract of JP 2001-302471, Oct. 31, 2001.
English language abstract of JP 2006-282524, Oct. 19, 2006.
English language abstract of JP 2008-074705, Apr. 3, 2008.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
Copending U.S. Appl. No. 12/976,093, filed Dec. 22, 2010.
Copending U.S. Appl. No. 12/976,124, filed Dec. 22, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 906, dated Aug. 29, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Oct. 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.

French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
French Search Report for FR 09/59388, dated Aug. 3, 2010.
French Search Report for FR 09/59391, dated Sep. 16, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed Dec. 10, 2010, in U.S. Appl. No. 12/642,599.
Notice of Allowance mailed Dec. 14, 2010, in U.S. Appl. No. 12/642,551.
Notice of Allowance mailed Dec. 15, 2010, in U.S. Appl. No. 12/642,637.
Notice of Allowance mailed Dec. 20, 2010, in U.S. Appl. No. 12/642,531.
Notice of Allowance mailed Dec. 20, 2010, in U.S. Appl. No. 12/642,575.
Notice of Allowance mailed Dec. 28, 2010, in U.S. Appl. No. 12/642,536.
Notice of Allowance mailed Dec. 29, 2010, in U.S. Appl. No. 12/642,480.
Notice of Allowance mailed Dec. 29, 2010, in U.S. Appl. No. 12/642,555.
Notice of Allowance mailed Dec. 8, 2010, in U.S. Appl. No. 12/642,473.
Notice of Allowance mailed in co-pending U.S. Appl. No. 12/339,753, dated Jul. 9, 2010.
Notice of Allowance mailed Jan. 28, 2011, in U.S. Appl. No. 12/642,592.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Nov. 30, 2010, in U.S. Appl. No. 12/642,624.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Dec. 17, 2010, in co-pending U.S. Appl. No. 12/642,451.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Nov. 22, 2010, in co-pending U.S. Appl. No. 12/642,593.
Office Action mailed Sep. 17, 2010, in co-pending U.S. Appl. No. 12/642,506.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
Copending U.S. Appl. No. 12/976,150, filed Dec. 22, 2010.
Copending U.S. Appl. No. 12/976,173, filed Dec. 22, 2010.
English language Abstract of DE 198 42 071, Mar. 16, 2000.
European Search Report for EP 10 19 5262, dated Apr. 1, 2011.
French Search Report for FR 09/59433, dated Sep. 24, 2010.
French Search Report for FR 09/59434, dated Sep. 24, 2010.
LookChem, poly[(dimethyliminio)-1,1,6-hexanediylchloride (1:2)], pp. 1-2, accesses Mar. 7, 2011.
Notice of Allowance mailed Apr. 1, 2011, in U.S. Appl. No. 12/642,506.
Notice of Allowance mailed Mar. 9, 2011, in U.S. Appl. No. 12/642,473.
Office Action mailed Jun. 8, 2011, in co-pending U.S. Appl. No. 12/339,781.
Office Action mailed Mar. 16, 2011, in co-pending U.S. Appl. No. 12/642,583.
P.R. Canterbery et al., International Cosmetic Ingredient Dictionary and Handbook, vol. 1, p. 759 (2002).
Ullmann's Encyclopedia of Industrial Chemistry, "Hair Preparations," Wiley-VCH Verlag GnbH & Co., KGaA, Weinheim, p. 20 (2006).

* cited by examiner

COMPOSITION FOR THE OXIDATION DYEING OF KERATIN FIBERS COMPRISING PARA-AMINOPHENOL, DIPROPYLENE GLYCOL AND AT LEAST ONE ADDITIONAL DYE PRECURSOR

This application claims benefit of U.S. Provisional Application No. 61/150,450, filed Feb. 6, 2009. This application also claims benefit of priority under 35 U.S.C. §119 to French Patent Application No. 0807306, filed Dec. 19, 2008.

The present application is related to a composition for the oxidation dyeing of keratin fibers.

It is known practice to dye keratin fibers, such as human hair, with dye compositions containing oxidation dyes, such as oxidation dye precursors and coloring modifiers.

Oxidation dye precursors, generally known as oxidation bases, are initially colorless or weakly colored compounds, which, in combination with oxidizing products, can give rise, via an oxidative condensation process, to colored and coloring compounds. They may be, in general, compounds such as ortho- or para-phenylenediamines, ortho- or para-aminophenols, and heterocyclic bases.

It is also known that it is possible to vary the shades obtained with these oxidation bases by combining them with couplers or coloring modifiers, the latter generally being chosen from, for example, meta-diaminobenzenes, meta-aminophenols, meta-diphenols, and certain heterocyclic compounds such as indole compounds.

The variety of the molecules involved as oxidation bases and couplers may make it possible to obtain a rich range of colors.

The "permanent" coloring that may be obtained by virtue of these oxidation dyes, also called oxidation dyeing, should, moreover, meet a certain number of requirements. Thus, it should have no toxicological drawbacks, it should allow shades to be obtained in the desired strength, and it should show good fastness with respect to external attacks such as light, bad weather, washing, permanent-waving, perspiration, and rubbing.

The dyes should also allow white hair to be covered and, finally, should be as nonselective as possible, i.e. they should make it possible to obtain the smallest possible differences in coloring along the length of the same keratin fiber, which is generally differently sensitized (i.e. damaged) between its end and its root.

Attempts have been made, in the hair-dyeing field, to improve the dyeing properties by the use, for example, of adjuvants. However, the choice of these adjuvants may be tricky in so far as they should improve the dyeing properties of the dye compositions without being detrimental to the other properties of these compositions. For example, adjuvants should not be detrimental to the keratin fiber-lightening properties and the coloring application properties.

The present disclosure is related to novel compositions for the oxidation dyeing of keratin fibers which may not have the drawbacks of the prior art. For example, one objective of the present disclosure is to obtain compositions for the oxidation dyeing of keratin fibers, which have improved dyeing properties which may make it possible to achieve the desired lightening and which may be easy to mix and to apply. The term "improved dyeing properties" is intended to mean, for example, an improvement in the level of strength/intensity and/or homogeneity of the dyeing.

This objective may be achieved by virtue of the present disclosure, which relates to a composition for the oxidation dyeing of keratin fibers, for example, human keratin fibers such as the hair, the composition intended to be mixed at the time of use with an oxidizing agent, comprising:

A) at least one oxidation base chosen from para-aminophenols and the addition salts thereof with an acid;
B) at least one additional dye precursor different from the at least one oxidation base defined in A); and
C) dipropylene glycol;

wherein:

the at least one oxidation base is present in an amount of greater than or equal to 1.5% by weight, relative to the total weight of the composition; and
the dipropylene glycol is present in an amount of greater than or equal to 3.5% by weight, relative to the total weight of the composition.

The composition according to the present disclosure may be produced without difficulty. It may not exhibit untimely crystallization of the dyes, for example, of the para-aminophenols.

The composition in accordance with the present disclosure may exhibit, after mixing with an oxidizing agent, improved dyeing properties. For example, the composition of the disclosure, which may be applied without difficulty to the keratin fibers, may result in colorings which exhibit good strength and/or intensity and/or good homogeneity of the color along the fiber between the end and the root of the hairs (also referred to as coloring selectivity) and/or good chromaticity.

Finally, the colorings obtained may be fast and may withstand the various external attacks that keratin fibers may be subjected to.

The present disclosure is also related to a process for dyeing keratin fibers using the composition disclosed herein.

The present disclosure is also related to a multicompartment device for using the composition disclosed herein.

The present disclosure is also related to the use of the composition disclosed herein for the oxidation dyeing of keratin fibers.

The composition of the present disclosure contains at least one oxidation base chosen from para-aminophenols and the addition salts thereof with an acid. By way of example of the para-aminophenol salts, non-limiting mention may be made of the hydrochlorides, hydrobromides, sulphates, citrates, succinates, tartrates, lactates, acetates, alkyl sulphates, and alkyl sulphonates.

Among the para-aminophenols that can be used according to the disclosure, non-limiting mention may be made, by way of example, of para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, and 4-amino-2-(β-hydroxyethylaminomethyl)phenol.

In at least one embodiment, the at least one oxidation base is chosen from para-aminophenol and 4-amino-3-methylphenol.

For example, the at least one oxidation base of the disclosure may be para-aminophenol.

According to at least one embodiment, the at least one oxidation base is for example present in an amount ranging from 1.5% to 10% by weight, such as from 1.5% to 5%, relative to the total weight of the composition.

The dipropylene glycol may for example be present in an amount ranging from 3.5% to 20% by weight, for example from 3.5% to 15%, such as from 5% to 15% by weight, relative to the total weight of the composition.

The composition according to the present disclosure comprises at least one additional dye precursor.

The at least one additional dye precursor is chosen from oxidation bases different than the at least one oxidation base chosen from para-aminophenols and the addition salts thereof with an acid, and couplers.

The at least one additional dye precursor may, for example, be chosen from oxidation bases chosen from those conventionally known in oxidation dyeing, among which non-limiting mention may be made of, for example, ortho- and para-phenylenediamines, double bases, ortho-aminophenols, heterocyclic bases, and also the addition salts thereof with an acid.

These oxidation bases may, for example, be cationic.

The para-phenylenediamines that can be used in the context of the present disclosure may, for example, be chosen from those of formula (I) below and the addition salts thereof with an acid:

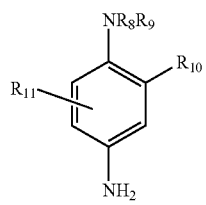

(I)

wherein:
- $R_8$ represents a hydrogen atom, a $C_1$-$C_4$ alkyl radical, a $C_1$-$C_4$ monohydroxyalkyl radical, a $C_2$-$C_4$ polyhydroxyalkyl radical, a $(C_1$-$C_4)$alkoxy$(C_1$-$C_4)$alkyl radical, or a $C_1$-$C_4$ alkyl radical substituted with a nitrogenous, phenyl, or 4'-aminophenyl group;
- $R_9$ represents a hydrogen atom, a $C_1$-$C_4$ alkyl radical, a $C_2$-$C_4$ polyhydroxyalkyl radical, a $(C_1$-$C_4)$alkoxy$(C_1$-$C_4)$alkyl radical, or a $C_1$-$C_4$ alkyl radical substituted with a nitrogenous group;
- $R_8$ and $R_9$ may also form, with the nitrogen atom which bears them, a nitrogenous heterocycle containing 5 or 6 ring members, optionally substituted with at least one alkyl, hydroxyl or ureido group;
- $R_{10}$ represents a hydrogen atom, a halogen atom such as a chlorine atom, or a $C_1$-$C_4$ alkyl, sulpho, carboxyl, $C_1$-$C_4$ monohydroxyalkyl or $C_1$-$C_4$ hydroxyalkoxy, $C_1$-$C_4$ acetylaminoalkoxy, $C_1$-$C_4$ mesylaminoalkoxy, or $C_1$-$C_4$ carbamoylaminoalkoxy radical;
- $R_{11}$ represents a hydrogen or halogen atom or a $C_1$-$C_4$ alkyl radical.

Among the nitrogenous groups of formula (I) above, non-limiting mention may, for example, be made of amino, mono$(C_1$-$C_4)$alkylamino, di$(C_1$-$C_4)$alkylamino, tri$(C_1$-$C_4)$alkylamino, monohydroxy$(C_1$-$C_4)$alkylamino, imidazolinium, and ammonium radicals.

Among the para-phenylenediamines of formula (I) above, non-limiting mention may, for example, be made of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-N,N-bis(β-hydroxyethyl)amino-2-methylaniline, N,N-bis(β-hydroxyethyl)-para-phenylenediamine, 4-N,N-bis(β-hydroxyethyl) amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N- (4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 2-methyl-1-N-β-hydroxyethyl-para-phenylenediamine, and the addition salts thereof with an acid.

Among the para-phenylenediamines of formula (I) above, non-limiting mention may, for example, also be made of para-phenylenediamine, para-toluoylenediamine, 2-isopropyl-para-phenylenediamine, 2-β-hydroxyethyl-para-phenylene -diamine, 2,6-dimethyl-para-phenylenediamine, 2,6-diethyl-para-phenylenediamine, 2,3-dimethyl-para-phenylenediamine, 2-chloro-para-phenylenediamine and N,N-bis(β-hydroxyethyl)-para-phenylenediamine, and the addition salts thereof with an acid.

Use, for example, may be made of para-phenylenediamine, para-toluoylenediamine, N,N-bis(β-hydroxyethyl)-para-phenylenediamine, and the addition salts thereof with an acid.

As used herein, the term "double bases" is intended to mean compounds comprising at least two aromatic rings on which amino and/or hydroxyl groups are carried.

Among the double bases that can be used as the at least one additional dye precursor in the composition in accordance with the present disclosure, non-limiting mention may, for example, be made of those corresponding to formula (II) below and the addition salts thereof with an acid:

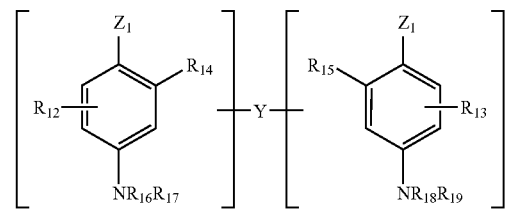

(II)

wherein:
- $Z_1$ and $Z_2$, which may be identical or different, represent a hydroxyl or —$NH_2$ radical that may be substituted with a $C_1$-$C_4$ alkyl radical or with a linker arm Y;
- the linker arm Y represents a linear or branched alkylene chain containing from 1 to 14 carbon atoms, that may be interrupted or terminated with at least one nitrogenous group and/or with at least one heteroatom such as oxygen, sulphur or nitrogen atoms, and optionally substituted with at least one hydroxyl or $C_1$-$C_6$ alkoxy radicals;
- $R_{12}$ and $R_{13}$ represent a hydrogen or halogen atom, a $C_1$-$C_4$ alkyl, $C_1$-$C_4$ monohydroxyalkyl, $C_2$-$C_4$ polyhydroxyalkyl or $C_1$-$C_4$ aminoalkyl radical, or a linker arm Y;
- $R_{14}$, $R_{15}$, $R_{16}$, $R_{17}$, $R_{18}$ and $R_{19}$, which may be identical or different, represent a hydrogen atom, a linker arm Y, or a $C_1$-$C_4$ alkyl radical;
- it being understood that the at least one additional dye precursor chosen from those of formula (II) comprises only one linker arm Y per molecule.

Among the nitrogenous groups in formula (II) above, non-limiting mention may, for example, be made of amino, mono (C$_1$-C$_4$)alkylamino, di(C$_1$-C$_4$)alkylamino, tri(C$_1$-C$_4$)alkylamino, monohydroxy(C$_1$-C$_4$)alkylamino, imidazolinium, and ammonium radicals.

Among the double bases of formulae (II) above, non-limiting mention may, for example, be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or an addition salt thereof with an acid, may, for example, be used.

The ortho-aminophenols that can be used as the at least one additional dye precursor in the context of the present disclosure may for example be chosen from 2-aminophenol, 2-amino-1-hydroxy-5-methylbenzene, 2-amino-1-hydroxy-6-methylbenzene, and 5-acetamido-2-aminophenol, and the addition salts thereof with an acid.

Among the heterocyclic bases that can be used as the at least one additional dye precursor in the composition in accordance with the disclosure, non-limiting mention may, for example. be made of pyridine derivatives, pyrimidine derivatives, and pyrazole derivatives, and the addition salts thereof with an acid.

Among the pyridine derivatives, non-limiting mention may, for example, be made of the pyridine derivatives described, for example, in patents GB 1 026 978 and GB 1 153 196, for instance 2,5-diaminopyridine, 2-(4-methoxyphenyl)amino-3-amino- pyridine, 2,3-diamino-6-methoxypyridine, 2-(β-methoxyethyl)amino-3-amino-6-methoxypyridine, and 3,4-diaminopyridine, and the addition salts thereof with an acid.

Among the pyrimidine derivatives, non-limiting mention may, for example, be made of the pyrimidine derivatives described, for example, in German patent DE 2 359 399 or Japanese patents JP 88-169 571 and JP 91-10659 or patent application WO 96/15765,for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin- 7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-imidazolylpropylaminopyrazolo[1,5-a]pyrimidine; the addition salts thereof and tautomeric forms thereof, when a tautomeric equilibrium exists.

Among the pyrazole derivatives, non-limiting mention may, for example, be made of the pyrazole derivatives described in patents DE 3 843 892 and DE 4 133 957 and patent applications WO 94/08969, WO 94/08970, FR-A-2 733 749 and DE 195 43 988, for instance 4,5-diaminopyrazoles, such as, for example, 4,5-diamino-1-methylpyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole; 3,4-diaminopyrazole; 4-amino-1,3-dimethyl-5-hydrazinopyrazole; 3,4,5-triaminopyrazoles such as, for example, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole; and the addition salts thereof with an acid.

For example, 4,5-diaminopyrazole, and for instance 4,5-diamino-1-(β-hydroxyethyl)pyrazole and/or an addition salt thereof may be used.

By way of pyrazole derivatives, non-limiting mention may also be made of diamino-N,N-dihydropyrazolopyrazolones and for example those described in application FR-A-2 886 136, such as the following pyrazole derivatives and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one.

For example, 2,3-diamino-6,7-dihydro-1H,5H-pyrazolo[1,2-a]pyrazol-1-one and/or an addition salt thereof may be used.

As heterocyclic bases, 4,5-diamino-1-(β-hydroxyethyl)pyrazole and/or 2,3-diamino-6,7-dihydro-1H,5H-pyrazolo[1,2-a]pyrazol-1-one and/or an addition salt thereof may, for example, be used.

As cationic oxidation bases that can be used in the compositions according to the disclosure, non-limiting mention may, for example, be made of the following cationic oxidation bases: para-phenylenediamines as, for example, described in patent applications FR-A-2 766 177 and FR-A-2 766 178, para-aminophenols as described, for example, in patent applications FR-A-2 766 177 and FR-A-2 766 178, ortho-phenylenediamines as described, for example, in patent applications FR-A-2 782 718, FR-A-2 782 716 and FR-A-2 782 719, ortho-aminophenols or double bases which are cationic, such as derivatives of bis(aminophenyl)alkylenediamine type, described in patent application FR-A-2 766 179, and also cationic heterocyclic bases, for example, bearing at least one quaternary nitrogen atom.

In at least one embodiment, the cationic oxidation bases that can be used in the compositions according to the disclosure are cationic para-phenylenediamines.

For example, in at least one embodiment, cationic oxidation bases of para-phenylenediamine structure, at least one of the amine functions of which is a tertiary amine bearing a pyrrolidine ring, the molecule having at least one quaternized nitrogen atom, may be used. Such bases are, for example, described in document EP-A-1 348 695.

According to at least one embodiment, the at least one additional dye precursor is chosen from para-phenylenediamine oxidation bases, heterocyclic bases, and the addition salts thereof with an acid.

When the at least one dye precursor is chosen from oxidation bases, the composition according to the present disclosure may, for example, comprise a total amount of oxidation bases different from the at least one oxidation base ranging from 0.0005% to 12% by weight, relative to the total weight of the composition. For example, it may comprise a total amount of oxidation bases different from the at least one oxidation base ranging from 0.005% to 8% by weight, such as from 0.05% to 5% by weight, relative to the total weight of the composition.

The at least one additional dye precursor may be chosen from couplers chosen from those conventionally used in oxidation dyeing compositions, i.e. meta-aminophenols, meta-phenylenediamines, meta-diphenols, naphthols and heterocyclic, couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

The at least one additional dye precursor may be chosen from couplers chosen for example from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo-[3,2-c]-1,2,4-triazole, and 2,6-dimethylpyrazolo-[1,5-b]-1,2,4-triazole, and the addition salts thereof with an acid.

When the at least one additional dye precursor is chosen from couplers, the composition according to the present disclosure may for example comprise a total amount of couplers ranging from 0.0001% to 15% by weight, relative to the total weight of the composition. For example, it may comprise a total amount of couplers ranging from 0.001% to 10% by weight, such as from 0.01% to 8% by weight, relative to the total weight of the composition.

The at least one additional dye precursor may be chosen from oxidation bases and couplers present in the compositions of the disclosure in the form of addition salts, such as in the form of addition salts thereof with an acid.

The addition salts with an acid that can be used in the context of the present disclosure may, for example, be chosen from the hydrochlorides, the hydrobromides, the sulphates, the citrates, the succinates, the tartrates, the lactates, the acetates, the alkyl sulphates, and the alkyl sulphonates.

When the oxidation bases or the couplers contain at least one carboxylic acid or sulphonic acid function, addition salts with a base can be envisaged. The addition salts with a base that can be used in the context of the compositions of the present disclosure may then for example be those obtained with sodium hydroxide, potassium hydroxide, aqueous ammonia, or amines.

According to at least one embodiment of the present disclosure, the composition comprises at least one coupler.

The composition of the present disclosure may further comprise at least one alkaline agent. The at least one alkaline agent may, for example, be chosen from aqueous ammonia, alkali carbonates or bicarbonates, alkanolamines such as mono-, di- and triethanolamines, and also derivatives thereof, oxyethylenated and/or oxypropylenated ethylenediamines, sodium hydroxide, potassium hydroxide, amino acids, and for example, basic amino acids such as arginine or lysine, and the compounds of formula (III) below:

wherein:
R is a propylene residue optionally substituted with a hydroxyl group or a $C_1$-$C_4$ alkyl radical;
$R_{22}$, $R_{23}$, $R_{24}$ and $R_{25}$, which may be identical or different, represent a hydrogen atom, a $C_1$-$C_4$ alkyl radical or a $C_1$-$C_4$ hydroxyalkyl radical.

According to one embodiment, the composition may comprise as the at least one alkaline agent at least one organic amine, for example, at least one alkanolamine. When the composition comprises at least one alkaline agent including an alkanolamine and ammonium hydroxides or their addition salts thereof, the amount of organic amine(s) may for example be higher than the amount of ammoniac.

According to at least one embodiment, the composition may comprise a small amount of aqueous ammonia, or even no aqueous ammonia. According to this embodiment, the composition may, for example, comprise at least one alkanolamine, such as monoethanolamine.

The composition described herein may also comprise at least one direct dye that may for example be chosen from nitrobenzene dyes, azo direct dyes, methine direct dyes, and the addition salts thereof. The at least one direct dye may be nonionic, anionic, or cationic.

The composition may also comprise other solvents constituting the dyeing medium. This dyeing medium may for example comprise, in addition to the dipropylene glycol, water or a mixture of water and at least one organic solvent other than dipropylene glycol, which is for example water-soluble.

As examples of the at least one organic solvent, non-limiting mention may for example be made of alcohols such as ethyl alcohol, isopropyl alcohol, benzyl alcohol and phenylethyl alcohol, or glycols or glycol ethers such as, for example, monomethyl, monoethyl or monobutyl ethers of ethylene glycol, propylene glycol or its ethers, such as, for example, propylene glycol monomethyl ether, butylene glycol, hexylene glycol and also diethylene glycol alkyl ethers such as, for example, diethylene glycol monoethyl ether or diethylene glycol monobutyl ether. The at least one organic solvent may be present in an amount ranging from 0.01% to 35% by weight, such as from 0.1% to 25% by weight, relative to the total weight of the composition.

In at least one embodiment, the compositions described herein may contain at least one additional organic solvent chosen from ethanol, propylene glycol, and hexylene glycol.

At the time of use, the composition described herein may be mixed with an oxidizing agent, for example, by mixing the composition described herein with a composition comprising at least one oxidizing agent.

The at least one oxidizing agent may be chosen, for example, from peroxides such as hydrogen peroxide, urea peroxide, bromates or ferricyanides of alkali metals, and persalts such as perborates, percarbonates, and persulphates. As the at least one oxidizing agent, for example, use may also be made of at least one oxidoreduction enzyme such as laccases, peroxidases, and 2-electron oxidoreductases (such as uricase), optionally in the presence of their respective donor or cofactor.

For instance, hydrogen peroxide may be used. The at least one oxidizing agent may for example be constituted of a solution of aqueous hydrogen peroxide, the titer of which may vary, for example, from 1 to 40 volumes, such as from 5 to 40 volumes.

According to at least one embodiment, the resultant composition after mixing with at least one oxidizing agent contains an amount of dipropylene glycol of greater than 0.5%.

According to at least one embodiment, the resultant composition after mixing with the at least one oxidizing agent contains at least 25% by weight of at least one fatty substance, such as at least 30% of at least one fatty substance.

The term "fatty substance" is intended to mean an organic compound which is insoluble in water at normal temperature (25° C.) and at atmospheric pressure (760 mmHg) (solubility less than 5%, for example, less than 1%, such as less than 0.1%). The fatty substances have, in their structure, at least one sequence of at least two siloxane groups or comprise at least one hydrocarbon-based chain containing at least 6 carbon atoms. In addition, the fatty substances are generally soluble in organic solvents under the same temperature and pressure conditions, for instance chloroform, ethanol, benzene, liquid petroleum jelly, and decamethylcyclopentasiloxane.

According to this embodiment, the composition comprises at least 25% by weight of at least one fatty substance other than fatty acids.

The at least one fatty substance may for example be chosen from lower alkanes, fatty alcohols, fatty acid esters, fatty alcohol esters, nonsilicone oils, such as mineral, plant, animal, or synthetic oils, nonsilicone waxes and silicones.

It is recalled that, for the purpose of the present disclosure, the alcohols, esters and fatty acids may for example have at least one saturated or unsaturated, linear or branched hydrocarbon-based group containing 6 to 30 carbon atoms, which is optionally substituted, for instance with at least one hydroxyl group (such as 1 to 4). If they are unsaturated, these compounds may comprise one to three conjugated or nonconjugated carbon-carbon double bonds.

With regard to the lower alkanes, they contain from 6 to 16 carbon atoms and are linear or branched, optionally cyclic. By way of example, the alkanes may be chosen from hexane and dodecane and isoparaffins such as isohexadecane and isodecane.

As nonsilicone oils that can be used in the composition of the present disclosure, non-limiting mention may, for example, be made of:
  hydrocarbon-based oils of animal origin, such as perhydrosqualene;
  hydrocarbon-based oils of plant origin, such as liquid triglycerides of fatty acids containing from 6 to 30 carbon atoms, for instance triglycerides of heptanoic acid or octanoic acid or alternatively, for example, sunflower oil, maize oil, soya oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names MIGLYOL® 810, 812 and 818 by the company Dynamit Nobel, jojoba oil, shea butter oil;
  linear or branched hydrocarbons of mineral or synthetic origin, containing at least 16 carbon atoms, such as liquid paraffins, petroleum jelly, liquid petroleum jelly, polydecenes, hydrogenated polyisobutene such as PARLEAM®;
  partially hydrocarbon-based fluoro oils; as fluoro oils, non-limiting mention may also be made of perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or else the bromoperfluorooctyl sold under the name FORALKYL® by the company Atochem; nonafluoromethoxybutane and nonafluoroethoxyisobutane; perfluoromorpholine derivatives, such as 4-trifluoromethyl perfluoromorpholine sold under the name PF 5052® by the company 3M.

The fatty alcohols that can be used in the composition of the present disclosure may be saturated or unsaturated, linear or branched, and contain 6 to 30 carbon atoms, such as from 8 to 30 carbon atoms; non-limiting mention may for example be made of cetyl alcohol, stearyl alcohol and the mixture thereof (cetylstearyl alcohol), octyldodecanol, 2-butyloctanol, 2-hexyldecanol, 2-undecylpentadecanol, oleyl alcohol, or linoleyl alcohol.

The wax(es) that can be used in the composition of the present disclosure may for example be chosen from carnauba wax, candelilla wax, esparto grass wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes, for instance beeswax, or modified beeswaxes (cerabellina); other waxes or waxy starting materials that can be used according to the present disclosure may for instance be marine waxes such as the product sold by the company Sophim under the reference M82, and polyethylene waxes or polyolefin waxes in general.

The esters may be esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being for example greater than or equal to 10.

Among the monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates; 2-ethylhexyl palmitate, 2-octyldecyl palmitate, alkyl myristates such as isopropyl myristate, butyl myristate, cetyl myristate, 2-octyldodecyl myristate, myrystyl myristate or stearyl myristate, hexyl stearate, butyl stearate, isobutyl stearate; dioctyl malate, hexyl laurate, and 2-hexyldecyl laurate.

In the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Non-limiting mention may also, for example, be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; and polyethylene glycol distearates.

Among the esters mentioned above ethyl palmitate, isopropyl palmitate, myristyl palmitate, cetyl palmitate, stearyl palmitate, 2-ethylhexyl palmitate, 2-octyldecyl palmitate, alkyl myristates such as isopropyl myristate, butyl myristate, cetyl myristate or 2-octyldodecyl myristate, hexyl stearate, butyl stearate, isobutyl stearate; dioctyl malate, hexyl laurate, 2-hexyldecyl laurate, isononyl isononanoate or cetyl octanoate may, for example, be used.

The composition may also comprise, as fatty ester, sugar esters and diesters of $C_6$-$C_{30}$, such as $C_{12}$-$C_{22}$, fatty acids. The term "sugar" is intended to mean oxygen-bearing hydrocarbon-based compounds containing several alcohol functions, with or without aldehyde or ketone functions, and which contain at least four carbon atoms. These sugars may be monosaccharides, oligosaccharides, or polysaccharides.

As suitable sugars, non-limiting mention may, for example, be made of sucrose (or saccharose), glucose, galactose, ribose, fucose, maltose, fructose, mannose, arabinose, xylose and lactose, and derivatives thereof, for example, alkyl derivatives, such as methyl derivatives, for instance methylglucose.

The sugar esters of fatty acids may be chosen, for example, from the group comprising the esters or mixtures of esters of sugars described previously and of linear or branched, saturated or unsaturated $C_6$-$C_{30}$, such as $C_{12}$-$C_{22}$, fatty acids. If they are unsaturated, these compounds may comprise one to three conjugated or nonconjugated carbon-carbon double bonds.

The esters according to this embodiment may also be chosen from mono-, di-, tri- and tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, for instance, oleo-palmitate, oleo-stearate and palmito-stearate mixed esters.

For example, monoesters and diesters such as sucrose, glucose or methylglucose mono- or dioleates, stearates, behenates, oleopalmitates, linoleates, linolenates and oleostearates may be used.

By way of example, mention may be made of the product sold under the name Glucate® DO by the company Amerchol, which is a methylglucose dioleate.

By way of examples of esters or mixtures of esters of sugar and fatty acid, non-limiting mention may also be made of the following:

the products sold under the names F160, F140, F110, F90, F70, SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name RYOTO SUGAR ESTERS, for example referenced B370 and corresponding to sucrose behenate formed from 20% monoester and 80% diester-triester-polyester;

the sucrose mono-dipalmito-stearate sold by the company Goldschmidt under the name TEGOSOFT® PSE.

The silicones that can be used in the composition of the present disclosure may be volatile or nonvolatile, cyclic, linear or branched silicones which are unmodified or modified with organic groups, having a viscosity from $5 \times 10^{-6}$ to 2.5 $m^2/s$ at 25° C., such as $1 \times 10^{-5}$ to 1 $m^2/s$.

The silicones that can be used in accordance with the present disclosure may be in the form of oils, waxes, resins, or gums.

For example, the silicone may be chosen from polydialkylsiloxanes, such as polydimethylsiloxanes (PDMS), and organomodified polysiloxanes comprising at least one functional group chosen from poly(oxyalkylene) groups, amino groups, and alkoxy groups.

The organopolysiloxanes are defined in greater detail in Walter Noll's "Chemistry and Technology of Silicones" (1968), Academie Press. They can be volatile or nonvolatile.

When they are volatile, the silicones may, for example, be chosen from those having a boiling point ranging from 60° C. to 260° C., such as:

(i) cyclic polydialkylsiloxanes containing from 3 to 7, such as from 4 to 5, silicon atoms. They may be for example octamethylcyclotetrasiloxane sold for instance under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of formula:

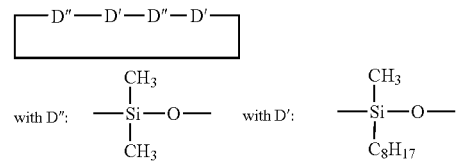

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ $m^2/s$ at 25° C. An example is decamethyltetrasiloxane sold, for example, under the name SH 200 by the company Toray Silicone. Silicones belonging to this category are also described in the article published in Cosmetics and Toiletries, Vol. 91, Jan. 76, pp. 27-32, Todd & Byers "Volatile Silicone fluids for cosmetics".

Nonvolatile polydialkylsiloxanes, polydialkylsiloxane gums and resins, polyorganosiloxanes modified with organofunctional groups above, and also mixtures thereof, may, for example, be used.

These silicones may for example be chosen from polydialkylsiloxanes, among which non-limiting mention may be made of polydimethylsiloxanes containing trimethylsilyl end groups. The viscosity of the silicones is measured at 25° C. according to ASTM standard 445 Appendix C.

Among these polydialkylsiloxanes, mention may be made, in a nonlimiting manner, of the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60,000 mm$^2$/s;

the VISCASIL® oils from General Electric and certain oils of the SF series (SF 96, SF 18) from General Electric.

Non-limiting mention may also be made of polydimethylsiloxanes containing dimethylsilanol end groups known under the name dimethiconol (CTFA), such as the oils of the 48 series from the company Rhodia.

In this category of polydialkylsiloxanes, non-limiting mention may also be made of the products sold under the names ABIL WAX® 9800 and 9801 by the company Goldschmidt which are poly($C_1$-$C_{20}$)dialkylsiloxanes.

The silicone gums that can be used in accordance with the present disclosure may, for example, be polydialkylsiloxanes, such as polydimethylsiloxanes with high number-average molecular masses ranging from 200,000 to 1,000,000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane, tridecane, and mixtures thereof.

Products that can, for example, be used in accordance with the present disclosure are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures of a polydimethylsiloxane gum and of a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane;

mixtures of two PDMSs with different viscosities, for instance, of a PDMS gum and of a PDMS oil, such as the product SF 1236 from the company General Electric. The product SF 1236 is a mixture of an SE 30 gum defined above, having a viscosity of 20 m$^2$/s, and an SF 96 oil, having a viscosity of 5×10$^{-6}$ m$^2$/s. This product may, for example, contain 15% SE 30 gum and 85% SF 96 oil.

The organopolysiloxane resins that can be used in accordance with the present disclosure may be crosslinked siloxane systems containing the following units:

$R_2SiO_{2/2}$, $R_3SiO_{1/2}$, $RSiO_{3/2}$ and $SiO_{4/2}$ wherein R represents an alkyl containing 1 to 16 carbon atoms. Among these products, the ones that may, for example, be used are those wherein R denotes a $C_1$-$C_4$ lower alkyl group, such as methyl.

Among these resins, non-limiting mention may be made of the product sold under the name DOW CORNING 593 or those sold under the names SILICONE FLUID SS 4230 and SS 4267 by the company General Electric, and which are silicones of dimethyl/trimethyl siloxane structure.

Non-limiting mention may also be made of the trimethylsiloxysilicate type resins sold, for example, under the names X22-4914, X21-5034, and X21-5037 by the company Shin-Etsu.

The organomodified silicones that can be used in accordance with the present disclosure may be silicones as defined above and may comprise in their structure at least one organofunctional group attached via a hydrocarbon-based group.

Besides the silicones described above, the organomodified silicones may be polydiarylsiloxanes, such as polydiphenylsiloxanes, and polyalkylarylsiloxanes functionalized with the organofunctional groups mentioned previously.

The polyalkylarylsiloxanes may be chosen for example from linear and/or branched polydimethyl/methylphenylsiloxanes and polydimethyl/diphenylsiloxanes with a viscosity ranging from 1×10$^{-5}$ to 5×10$^{-2}$ m$^2$/s at 25° C.

Among these polyalkylarylsiloxanes, non-limiting mention may, by way of example, be made of the products sold under the following names:

the SILBIONE® oils of the 70 641 series from Rhodia;

the oils of the RHODORSIL® 70 633 and 763 series from Rhodia;

the oil DOW CORNING 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 from the company Union Carbide, and the ($C_{12}$)alkylmethicone copolyol sold by the company Dow Corning under the name Q2 5200;

substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups may, for example, be $C_1$-$C_4$ aminoalkyl groups;

alkoxylated groups such as the product sold under the name SILICONE COPOLYMER F-755 by SWS Silicones, and ABIL WAX® 2428, 2434 and 2440 by the company Goldschmidt.

For example, the at least one fatty substance may be non-oxyalkylenated and nonglycerolated.

For example, the at least one fatty substance may be chosen from compounds that are liquid or pasty at ambient temperature and at atmospheric pressure.

For example, the at least one fatty substance may be a compound that is liquid at a temperature of 25° C. and at atmospheric pressure.

According to at least one embodiment, the at least one fatty substance may be chosen from liquid petroleum jelly, polydecenes, liquid esters of fatty acids or of fatty alcohols, and mixtures thereof; for example, the at least one fatty substance of the composition according to the present disclosure may be non-silicone-based.

The composition in accordance with the present disclosure may also comprise at least one adjuvant conventionally used in hair-dyeing compositions.

The term "adjuvant" is intended to mean an additive other than the abovementioned compounds.

As examples of adjuvants that can be used, non-limiting mention may be made of anionic, cationic, nonionic, amphoteric or zwitterionic surfactants, or mixtures thereof; anionic, cationic, nonionic, amphoteric or zwitterionic polymers, inorganic or organic thickeners, such as anionic, cationic, nonionic and amphoteric associative polymeric thickeners, other than the associative celluloses according to the present disclosure; antioxidants or reducing agents, penetrating agents; sequestering agents; fragrances; buffers; dispersing agents; conditioning agents such as, for example, volatile or nonvolatile silicones, which may be modified or unmodified; film-forming agents; ceramides; preservatives; opacifiers; and antistatic agents.

The above adjuvants may in general be present in an amount, for each of them, ranging from 0.01% to 20% by weight, relative to the weight of the composition.

Of course, those skilled in the art will take care to select the optional adjuvant(s) mentioned above in such a way that the beneficial properties intrinsically associated with the compositions according to the present disclosure are not, or not substantially, impaired by the addition(s) envisaged.

The pH of the composition in accordance with the present disclosure may, for example, range from 3 to 12, for instance, from 5 to 11, such as from 7 to 11. It may be adjusted to the desired value via use of acidifying or basifying agents normally used in the dyeing of keratin fibers, or alternatively via use of conventional buffer systems.

The alkaline agents may, for example, be those previously described herein.

Among the acidifying agents, non-limiting mention may be made, as examples, of inorganic or organic acids such as hydrochloric acid, ortho-phosphoric acid, carboxylic acids such as tartaric acid, citric acid or lactic acid, and sulphonic acids.

The composition according to the present disclosure may be in various forms, such as in the form of liquids, creams or gels, or in any other form suitable for dyeing keratin fibers, such as human hair.

The present disclosure also relates to a process for dyeing keratin fibers, comprising:
combining at least one composition for the oxidation dyeing of keratin fibers, comprising:
  A) at least one oxidation base chosen from para-aminophenols and the addition salts thereof with an acid;
  B) at least one additional dye precursor different from the at least one oxidation base defined in A); and
  C) dipropylene glycol;
  wherein:
    the at least one oxidation base is present in an amount of greater than or equal to 1.5% by weight, relative to the total weight of the composition; and
    the dipropylene glycol is present in an amount of greater than or equal to 3.5% by weight, relative to the total weight of the composition;
  with at least one composition comprising at least one oxidizing agent;
applying the resultant composition to the keratin fibers; and
leaving the resultant composition on the keratin fibers for a period of time sufficient to develop the desired coloration.

The process of the present disclosure is thus a process wherein the composition disclosed herein is mixed with a composition comprising at least one oxidizing agent, and the resultant mixture is applied to the keratin fibers. The color may be revealed at acidic, neutral, or alkaline pH and the at least one oxidizing agent may be added just at the time of use or it may be used simultaneously with or sequentially to the other elements of the composition disclosed herein.

After a leave-on time which may range, for example, from 1 to 60 minutes, such as from 5 to 45 minutes, the keratin fibers may be rinsed, optionally washed with shampoo and rinsed again, and then dried.

The process of the present disclosure can be carried out using 2 or 3 compositions, wherein one composition comprises at least one oxidation base as defined herein, at least one additional dye precursor, dipropylene glycol, and, optionally, at least one alkaline agent; and a second composition comprises at least one oxidizing agent and, optionally, at least one fatty substance, it being possible for the at least one fatty substance to be completely or partly contained in a third composition.

Thus, the present disclosure is also related to a multicompartment dyeing device or dyeing "kit" comprising:
a first compartment containing at least one composition comprising:
  A) at least one oxidation base chosen from para-aminophenol and the addition salts thereof with an acid;
  B) at least one additional dye precursor different from the at least one oxidation base defined in A);
  C) dipropylene glycol; and
  D) optionally, at least one alkaline agent;
  wherein:
    the at least one oxidation base is present in an amount of greater than or equal to 1.5% by weight, relative to the total weight of the composition; and
    the dipropylene glycol is present in an amount of greater than or equal to 3.5% by weight, relative to the total weight of the composition; and
a second compartment comprising:
at least one oxidizing agent; and
optionally, at least one fatty substance.

According to another embodiment, the multicompartment dyeing device disclosed herein comprises
a first compartment containing at least one composition comprising:
  A) at least one oxidation base chosen from para-aminophenol and the addition salts thereof with an acid;
  B) at least one additional dye precursor different from the at least one oxidation base defined in A);
  C) the dipropylene glycol; and
  D) optionally, at least one alkaline agent,
  wherein:
    the at least one oxidation base is present in an amount of greater than or equal to 1.5% by weight, relative to the total weight of the composition; and the dipropylene glycol is present in an amount of greater than or equal to 3.5% by weight, relative to the total weight of the composition;

a second compartment comprising at least one oxidizing agent; and a third compartment containing at least one fatty substance.

In at least one embodiment, the composition comprising the at least one fatty substance may be anhydrous. For the purpose of the present disclosure, the term "anhydrous composition" is intended to mean a cosmetic composition having a water content of less than 5% by weight, for example, less than 2% by weight, such as less than 1% by weight, relative to the weight of the anhydrous composition. It should be noted that this water may, for example, be bound water, such as the water from the crystallization of the salts or traces of water absorbed by the starting materials used in the preparation of the compositions according to the present disclosure.

The present disclosure is also related to the use of a composition as defined above, for the oxidation dyeing of keratin fibers, for example human keratin fibers such as the hair.

The present disclosure is further related to a method for making a composition for the oxidation dyeing of keratin fibers comprising combining:

A) at least one oxidation base chosen from para-aminophenols and the addition salts thereof with an acid;
B) at least one additional dye precursor different from the at least one oxidation base defined in A); and
C) dipropylene glycol;

wherein:
the at least one oxidation base is present in an amount of greater than or equal to 1.5% by weight, relative to the total weight of the composition; and
the dipropylene glycol is present in an amount of greater than or equal to 3.5% by weight, relative to the total weight of the composition The examples which follow are intended to illustrate the present disclosure without, however, limiting the scope thereof.

In these examples, all the amounts are indicated as percent by weight of active material (AM) relative to the total weight of the composition, unless otherwise indicated.

EXAMPLES

The following compositions were prepared:

Example 1

| Composition 1 | Concentration (g %) |
|---|---|
| Disteardimonium hectorite | 3 |
| Octyldodecanol | 11.5 |
| Glycol distearate | 8 |
| Liquid petroleum jelly | 64.5 |
| Propylene carbonate | 1 |
| Laureth-2 | 1 |
| Polysorbate 21 | 11 |

| Composition 2 | Concentration (g %) |
|---|---|
| Diethylenetriaminepentaacetic acid, pentasodium salt as an aqueous solution at 40% | 1 AS IS |
| Sodium metabisulphite | 0.7 |
| Monoethanolamine | 14.5 |
| 1-methyl-2,5-diaminobenzene | 1.69 |
| 1-methyl-2-hydroxy-4-beta-hydroxyethylaminobenzene | 4.17 |
| 4-amino-2-hydroxytoluene | 1.39 |
| 1,3-dihydroxybenzene (resorcinol) | 0.88 |
| p-aminophenol | 2.43 |
| NATROSOL 250 HHR (hydroxyethylcellulose) | 1.5 |
| Dipropylene glycol | 10 |
| Ethanol | 15 |
| Propylene glycol | 5 |
| Ascorbic acid | 0.25 |
| Water | Qs 100 g |

| Composition 3 | Concentration (g %) |
|---|---|
| Diethylenetriaminepentaacetic acid, pentasodium salt as an aqueous solution at 40% | 0.15 AS IS |
| Hydrogen peroxide in solution at 50% (200 vol. aqueous hydrogen peroxide) | 12 AS IS |
| Sodium stannate | 0.04 |
| Sodium pyrophosphate | 0.03 |
| Liquid petroleum jelly | 20 |
| hexadimethrine chloride (AM at 60% in water) | 0.25 AS IS |
| Polyquaternium-6 (AM at 40% in water) | 0.5 AS IS |
| Glycerol | 0.5 |
| Cetylstearyl alcohol (C16/C18 30/70) | 8 |
| Oxyethylenated cetylstearyl alcohol (33 EO) | 3 |
| Protected oxyethylenated (4 EO) rapeseed acid amide at 92.3% in water | 1.3 AS IS |
| Vitamin E | 0.1 |
| Phosphoric acid | Qs pH 2.2 |
| Water | QS 100 |

Example 2

| Composition 1 | MP code | Concentration (g %) |
|---|---|---|
| Disteardimonium hectorite | 2177 | 3 |
| Octyldodecanol | 1092 | 11.5 |
| Glycol distearate | 1122 | 8 |
| Liquid petroleum jelly | 145 B | 64.5 |
| Propylene carbonate | 52585 | 1 |
| Laureth-2 | 1178 D2 | 1 |
| Polysorbate 21 | 53608 | 11 |

| Composition 2 | Concentration (g %) |
|---|---|
| Diethylenetriaminepentaacetic acid, pentasodium salt as an aqueous solution at 40% | 1 AS IS |
| Sodium metabisulphite | 0.7 |
| Monoethanolamine | 14.5 |
| 1-methyl-2,5-diaminobenzene | 0.464 |
| 1-methyl-2-hydroxy-4-beta-hydroxyethylaminobenzene | 0.58 |
| 4-amino-2-hydroxytoluene | 0.087 |
| 1,3-dihydroxybenzene (RESORCINOL) | 0.435 |
| p-aminophenol | 1.56 |
| 2-methyl-1,3-dihydroxybenzene | 1.16 |
| 2-amino-3-hydroxypiridine | 0.145 |
| 6-hydroxyindole | 0.174 |
| NATROSOL 250 HHR (hydroxyethylcellulose) | 1.5 |
| Dipropylene glycol | 10 |

| Composition 2 | Concentration (g %) |
|---|---|
| Ethanol | 15 |
| Hexylene glycol | 5 |
| Ascorbic acid | 0.25 |
| Water | Qs 100 g |

| Composition 3 | Concentration (g %) |
|---|---|
| Diethylenetriaminepentaacetic acid, pentasodium salt as an aqueous solution at 40% | 0.15 AS IS |
| Hydrogen peroxide in solution at 50% (200 vol. aqueous hydrogen peroxide) | 12 AS IS |
| Sodium stannate | 0.04 |
| Sodium pyrophosphate | 0.03 |
| Liquid petroleum jelly | 20 |
| Hexadimethrine chloride (AM at 60% in water) | 0.25 AS IS |
| Polyquaternium-6 (AM at 40% in water) | 0.5 AS IS |
| Glycerol | 0.5 |
| Cetylstearyl alcohol (C16/C18 30/70) | 8 |
| Oxyethylenated cetylstearyl alcohol (33 EO) | 3 |
| Protected oxyethylenated (4 EO) rapeseed acid amide at 92.3% in water | 1.3 |
| Vitamin E | 0.1 |
| Phosphoric acid | Qs pH 2.2 |
| Water | QS 100 |

For each of Examples 1 and 2, compositions 1, 2, and 3 were mixed at the time of use in the following proportions: 10 g of composition 1 with 4 g of composition 2 and 16 g of composition 3. The resultant mixture was applied to locks of natural grey hair containing 90% of white hairs, in a bath ratio of 10 g of mixture per 1 g of hair. After a leave-on time of 30 minutes, the hair was rinsed, washed with a standard shampoo, and dried.

The hair coloring was evaluated visually. The results obtained are provided in the following table:

|  | Hair Coloring | Hair Coloring |
|---|---|---|
| Example 1 | Dark brown | Mahogany red |
| Example 2 | Blond | Golden coppery |

Example 3

Compositions 2 and 3 of Example 2 were mixed weight for weight, and the resultant mixture was applied to natural or permanent-waved grey hair containing 90% white hairs, in a bath ratio of 10 g of mixture per 1 g of hair.

After a leave-on time of 30 minutes, the hair was rinsed, washed with a standard shampoo, and dried. A relatively nonselective coloring was obtained.

What is claimed is:

1. A composition for the oxidation dyeing of keratin fibers, comprising:
    A) at least one oxidation base chosen from para-aminophenols and the addition salts thereof with an acid;
    B) at least one additional dye precursor different from the at least one oxidation base defined in A); and
    C) dipropylene glycol;
    wherein:
    the at least one oxidation base is present in an amount of greater than or equal to 1.5% by weight, relative to the total weight of the composition; and
    the dipropylene glycol is present in an amount of greater than or equal to 3.5% by weight, relative to the total weight of the composition.

2. The composition according to claim 1, wherein the at least one oxidation base is chosen from para-aminophenol and 4-amino-3-methylphenol.

3. The composition according to claim 2, wherein the at least one oxidation base is para-aminophenol.

4. The composition according to claim 1, wherein the at least one oxidation base is present in an amount ranging from 1.5% to 10% by weight, relative to the total weight of the composition.

5. The composition according to claim 4, wherein the at least one oxidation base is present in an amount ranging from 1.5% to 5% by weight, relative to the total weight of the composition.

6. The composition according to claim 1, wherein the dipropylene glycol is present in an amount ranging from 3.5% to 20% by weight, relative to the total weight of the composition.

7. The composition according to claim 6, wherein the dipropylene glycol is present in an amount ranging from 3.5% to 15% by weight, relative to the total weight of the composition.

8. The composition according to claim 7, wherein the dipropylene glycol is present in an amount ranging from 5% to 15% by weight, relative to the total weight of the composition.

9. The composition according to claim 1, wherein the at least one additional dye precursor is chosen from oxidation bases and couplers.

10. The composition according to claim 9, wherein the at least one additional dye precursor is chosen from ortho- and para-phenylenediamine oxidation bases, double bases, ortho-aminophenols, heterocyclic bases, and the addition salts thereof with an acid.

11. The composition according to claim 10, wherein the at least one additional dye precursor is chosen from para-phenylenediamine oxidation bases, heterocyclic bases, and the addition salts thereof with an acid.

12. The composition according to claim 9, wherein the at least one additional dye precursor is chosen from meta-aminophenol couplers, meta-phenylenediamines, meta-diphenols, naphthols, heterocyclic couplers, and the addition salts thereof with an acid.

13. The composition according to claim 12, wherein the at least one additional dye precursor is chosen from meta-aminophenols and meta-phenylenediamines.

14. The composition according to claim 1, further comprising at least one alkaline agent.

15. The composition according to claim 14, wherein the at least one alkaline agent is chosen from ammonia and alkanolamine.

16. The composition according to claim 15, wherein the at least one alkaline agent is alkanolamine.

17. The composition according to claim 1, further comprising at least one additional organic solvent chosen from ethanol, propylene glycol, and hexylene glycol.

18. A process for dyeing keratin fibers, comprising:
    combining at least one composition for the oxidation dyeing of keratin fibers, comprising:
    A) at least one oxidation base chosen from para-aminophenols and the addition salts thereof with an acid;
    B) at least one additional dye precursor different from the at least one oxidation base defined in A); and
    C) dipropylene glycol;

wherein:
the at least one oxidation base is present in an amount of greater than or equal to 1.5% by weight, relative to the total weight of the composition; and
the dipropylene glycol is present in an amount of greater than or equal to 3.5% by weight, relative to the total weight of the composition;
with at least one composition comprising at least one oxidizing agent;
applying the resultant composition to the keratin fibers; and
leaving the resultant composition on the keratin fibers for a period of time sufficient to develop the desired coloration.

19. A multicompartment device comprising:
a first compartment containing at least one composition comprising:
A) at least one oxidation base chosen from para-aminophenol and the addition salts thereof with an acid;
B) at least one additional dye precursor different from the at least one oxidation base defined in A);
C) dipropylene glycol; and
D) optionally, at least one alkaline agent;
wherein:
the at least one oxidation base is present in an amount of greater than or equal to 1.5% by weight, relative to the total weight of the composition; and
the dipropylene glycol is present in an amount of greater than or equal to 3.5% by weight, relative to the total weight of the composition; and
a second compartment comprising:
at least one oxidizing agent; and
optionally, at least one fatty substance.

20. A method for making a composition for the oxidation dyeing of keratin fibers comprising combining:
A) at least one oxidation base chosen from para-aminophenols and the addition salts thereof with an acid;
B) at least one additional dye precursor different from the at least one oxidation base defined in A); and
C) dipropylene glycol;
wherein:
the at least one oxidation base is present in an amount of greater than or equal to 1.5% by weight, relative to the total weight of the composition; and
the dipropylene glycol is present in an amount of greater than or equal to 3.5% by weight, relative to the total weight of the composition.

\* \* \* \* \*